United States Patent [19]

Stern et al.

[11] 4,109,647
[45] Aug. 29, 1978

[54] METHOD OF AND APPARATUS FOR MEASUREMENT OF BLOOD FLOW USING COHERENT LIGHT

[75] Inventors: Michael D. Stern, Rockville; Donald L. Lappé, Baltimore, both of Md.

[73] Assignee: The United States of America as represented by the Secretary of the Department of Health, Education and Welfare, Washington, D.C.

[21] Appl. No.: 778,083

[22] Filed: Mar. 16, 1977

[51] Int. Cl.² ............................................. G01P 3/36
[52] U.S. Cl. ................................. 128/2.05 F; 356/28
[58] Field of Search ................. 128/2 L, 2.05 F, 2 A; 356/28, 39–40, 41; 250/573

[56] References Cited

U.S. PATENT DOCUMENTS

| | | | |
|---|---|---|---|
| 3,313,290 | 3/1967 | Chance | 128/2 A |
| 3,511,227 | 2/1967 | Johnson | 128/2.05 F |
| 3,532,427 | 10/1970 | Paine | 356/28 |
| 3,552,855 | 1/1971 | Crosswy et al. | 356/28 |
| 3,584,956 | 6/1971 | Hines | 356/28 |
| 3,647,299 | 3/1972 | Lavalee | 356/41 |
| 3,709,599 | 1/1973 | Iten | 356/28 |
| 3,795,447 | 3/1974 | Welch et al. | 356/28 |
| 3,814,081 | 3/1972 | Mori | 128/2 L |
| 3,830,222 | 8/1974 | Chance | 128/2 A |

OTHER PUBLICATIONS

Foreman, J. W. Jr. et al., "Fluid Flow Measurements with a Laser Doppler Velocimeter", IEEE Jrnl. Quantum Elec. QE-2, #8, Aug. 1966, pp. 260–266.

Chance, Britton et al., "A Time-Sharing Instrument for Direct Readout of Oxidation-Reduction States in Intra-cellular Compartments of Cardiac Tissue", IEEE Transactions on Biomed Egnr., vol. BME-17, No. 2, Apr. 1970, pp. 118–120.

Stern, N. D., "In-Vivo Evaluation of Micro-circulation by Coherent Light Scattering", Nature vol. 254, Mar. 6, 1975, pp. 56–58.

Primary Examiner—Robert W. Michell
Assistant Examiner—Francis J. Jaworski
Attorney, Agent, or Firm—Browdy and Neimark

[57] ABSTRACT

An apparatus for measuring the flow parameter of blood flowing in an organ includes a laser and associated optics which effect the illumination of tissues. The laser light, scattered by the tissues, emerges with a spectrum broadened by Doppler effect due to motion of red blood cells in the micro-circulation vessels. The light from the tissues is fed to a photomultiplier tube or photodiode via a pinhole mask and interference filter. The photomultiplier tube or photodiode, as a result of beating of various components of the light it receives, produces as its output signals a homodyne or heterodyne spectrum or both. These output signals are fed, via a low pass filter, to a differentiator, which differentiates the output signals from the multiplier tube or photodiode, which are passed by the filter, with respect to time. The output of the differentiator is fed to a root-mean-square (RMS) detector. The low pass filter passes, for example, signals having a frequency up to about 20 KHz. The output (R) from the detector, which represents the blood flow (average percolation) in the tissues plus shot noise, a constant (S), is fed to a digital voltmeter. The voltmeter produces a visible read-out indicative of the output from the detector. The output from the detector is also fed to a calculating circuit which also receives a signal corresponding to the mean current (I) produced by the photomultiplier or photodiode, the calculating circuit effecting a solution to the equation $$F_{norm} = \frac{\sqrt{R^2 - SI}}{I}$$

$F_{norm}$ is a normalized output signal representation of blood flow parameter.

39 Claims, 9 Drawing Figures

METHOD OF AND APPARATUS FOR MEASUREMENT OF BLOOD FLOW USING COHERENT LIGHT

BACKGROUND OF THE INVENTION

This invention relates to a method of an apparatus for measuring the flow of red blood cells flowing in a microvascular bed. The present invention relates, more particularly, to a method of an apparatus for measuring the flow of red blood cells flowing in a microvascular bed, using the Doppler scattering of coherent light. The invention can be practiced in connection with the measuring of the blood flow parameters of kidney tissues, brain tissues, liver tissues, tissues of other organs, and local cutaneous tissues, as well.

The study of pharmacologic agents and pathophysiologic states requires a technique of measuring the tissue blood flow in internal organs, in the microvascular bed of the skin and the like, its distribution in different regions of the tissues, and its variation with time. This is especially true in the kidney, where interarenal redistribution of flow is one of the major effects of drugs and hemodynamic changes.

Known techniques of measuring regional renal blood flow include radioactive indicator washout, implanted hydrogen electrode indicator dilution technique, autoradiography, angiography, implantation of $\beta$-ray detectors and radioactive microsphere trapping. Each of these known techniques has serious drawbacks for the monitoring of tissue perfusion during physiologic experiments. The radioactive tracer washout can be used dynamically, but there is doubt as to the localization of the abstract compartments which it defines, and whether this localization is the same in all physiologic states. The hydrogen electrode method is invasive, and may cause alterations in local flow. The same applies to implantable radiation detectors. The radioactive microsphere method is precise and localized, but it is destructive, and only a small number of data points may be taken in a single subject. It cannot be used to study dynamic changes in real time. The same is true of autoradiography. Angiography is not quantitative and requires the injection of contrast media which may disturb renal function.

It has been proposed in U.S. Pat. No. 3,511,227 to C. C. Johnson entitled "Measurement of Blood Flow Using Coherent Light" issued May 12, 1970 that the rate of blood flow within a blood vessel can be determined by measuring the Doppler frequency shift of coherent radiation, which can be produced by a laser, by directing a coherent light beam into the blood stream of a patient, and comparing the frequency of the scattered light radiation with the frequency of the original beam, the difference being a measure of the blood flow rate. This technique may be suitable for measuring the flow rate within a relatively large vessel, using an optical catheter or needle, or in some cases, by selecting a given wavelength which will penetrate the vessel with a venipuncture. On the other hand, the technique cannot be used accurately to measure the velocity of motion of red blood cells in a microvascular bed of an organ, for example, to measure the local renal cortical blood flow parameter or the local cutaneous blood flow parameter.

It has been reported, on the basis of preliminary experiments, that if the coherent monochromatic light of a laser is used to illuminate tissues, the light scattered from the tissue has a broadened spectrum. The broadening is believed to be a result of the Doppler frequency shift sustained by light when it is scattered from red cells moving in the microvessels. See Stern, "In vivo evaluation of microcirculation by coherent light scattering", *Nature,* Vol. 254, pages 56–58, March 1975.

SUMMARY OF THE INVENTION

It is the principal object of the present invention to provide a method of and apparatus for measuring the flow of moving material which utilize the reported phenomenon of spectrum broadening of coherent monochromatic light scattered from the material.

It is an object of the present invention to provide a method of and apparatus for measuring blood flow in tissue having a vascular bed which do not require the use of radioactive materials.

It is another object of the present invention to provide a method of and an apparatus for measuring blood flow in tissue having a vascular bed which avoid invasive procedures of the site.

It is an additional object of the present invention to provide an apparatus for and a method of measuring blood flow in tissue having a vascular bed which can be continuous and effects a quantitative measure of the flow.

It is a further object of the present invention to provide an apparatus for and method of measuring blood flow in tissue having a vascular bed which involves the use of the coherent monochromatic light of a laser.

It is yet another object of the present invention to provide an apparatus for and a method of measuring blood flow in tissue having a microvascular bed which determine blood flow as a function of Doppler frequency shifts of coherent monochromatic light scattered from red blood cells moving in microvessels in the bed.

It is yet an additional object of the present invention to provide an apparatus for and a method of measuring the flow of blood flowing in tissue which utilize the reported phenomenon of spectrum broadening of coherent monochromatic light scattered from tissues.

The foregoing objects, as well as others which are to become apparent from the text below, are achieved in accordance with an exemplary embodiment of the present invention, in its apparatus aspect, by providing a continuous wave laser, optics for illuminating a region of tissue, optics for retrieving scattered light, a pinhole mask for selecting one coherence area of the scattering pattern, a filter to protect against room light, a photodetector such as a photomultiplier tube or a photodiode and circuitry for processing and analyzing the output of the photo-detector. The circuitry includes, a differentiator, a low pass filter and a weighted averaging detector, preferably a root-mean-square (RMS) detector, connected in cascade between the photo-detector and a flow parameter calculating circuit. The flow parameter calculating circuit also receives a second output from a linear, averaging amplifier coupled between the calculating circuit and the photo-detector, this amplifier providing an output signal representative of the mean current from the photo-detector. The calculating circuit is designed to solve the equation $F = \sqrt{R^2 - SI}$, where $R$ is the output from the RMS detector, and $S$ is a constant representing shot noise and $I$ is the mean photo-detector current of the photo-detector.

In a preferred variant the calculating circuit also effects an arithmetic division of F by I, providing $F_{norm}$, the normalized flow parameter.

The method of the present invention can be carried out using the above-described apparatus. The method involves illuminating a region of tissue having a vascular bed with coherent light; retrieving light scattered by the tissue, this light having a broadened spectrum caused by moving blood cells in the tissue; producing a reduced frequency spectrum of signals by beating the received light signals in a nonlinear photo-detector; passing the reduced frequency spectrum of signals through a low-pass filter and a differentiator; obtaining a weighted average R of the frequency spectrum of signals passed through the differentiator, preferably obtaining the RMS valve thereof; determining the mean current I produced by the nonlinear photo-detector; and performing the following calculation: $F = \sqrt{R^2 - SI}$ where F is the flow parameter and S is a constant determined by the gain of the photo-detector.

In a preferred variant of the method F is divided by I to provide $F_{norm}$, the normalized flow parameter.

The present invention, in its apparatus aspect, is broadly characterized by means for sensing backscattered light from moving material, means for determining the spectrum broadening of the sensed backscattered light and circuitry which processes signals produced to develop a signal representative of flow parameter.

In its method aspect, the present invention is broadly characterized by sensing the backscattered light, determining the spectrum broadening and developing a signal representation of flow parameter.

DESCRIPTION OF THE PREFERRED EMBODIMENTS

Figure 1:
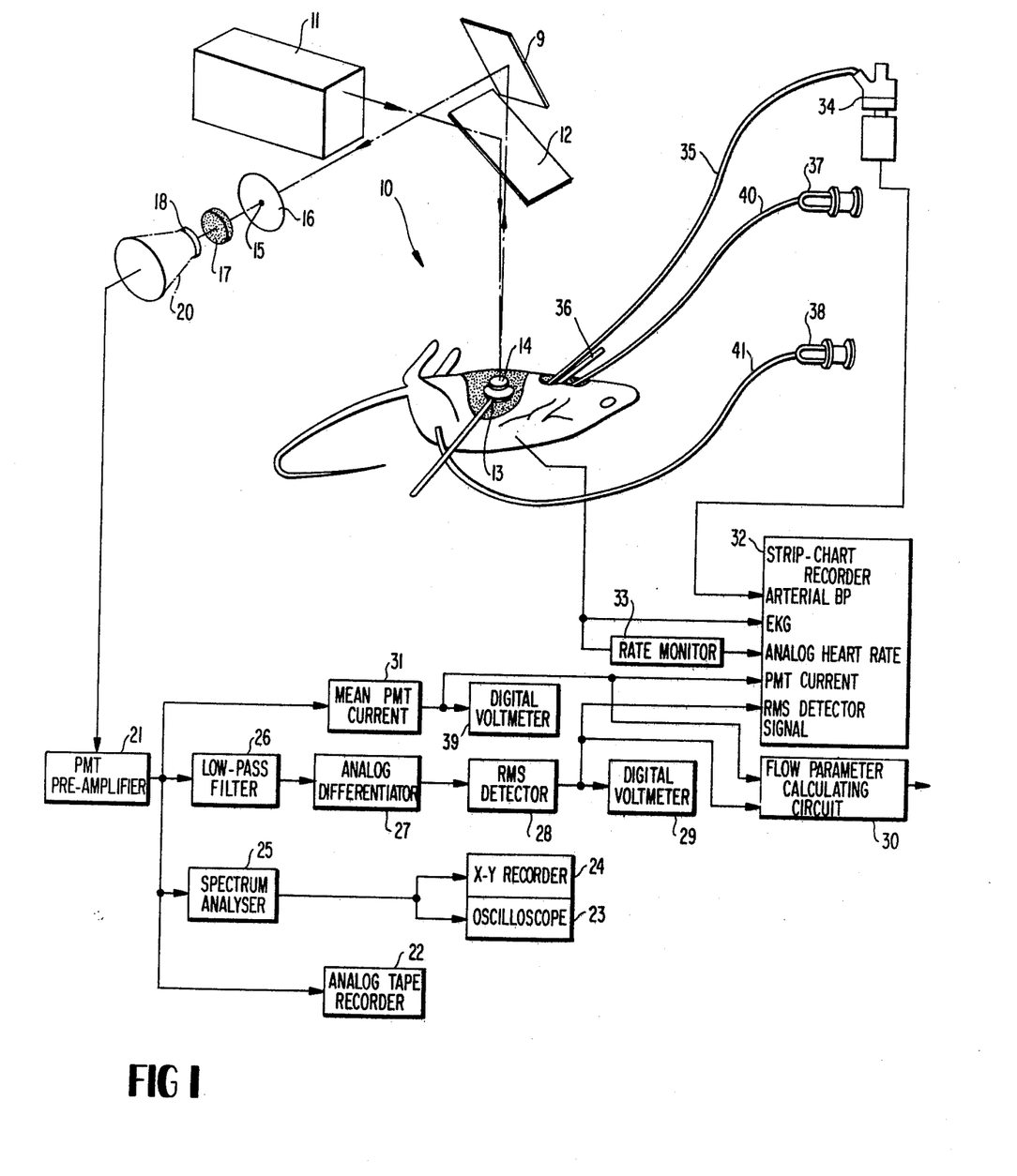
FIG. 1 is a schematic diagram of an experimental set-up used in studying local blood flow in the outer cortex of a rat kidney using laser Doppler spectroscopy and incorporating an exemplary embodiment of an apparatus according to the present invention.

Before turning to FIG. 1 and a consideration in detail of the experimental set-up shown therein, which set-up incorporates an embodiment of an apparatus for measuring the flow parameter of blood flowing in tissue, a brief consideration of the principles upon which the present invention is based is in order.

When coherent light, as a practical matter supplied by a suitable laser, is scattered by a moving blood cell, its frequency is altered by an amount $\Delta\omega = \vec{K}\cdot\vec{v}$ where $\vec{K}$ and $\vec{v}$ are respectively the scattering vector of the light and the velocity vector of the red cell. The superimposition of the light scattered by red cells of different velocities and at different angles gives rise to an overall broadening of the spectral line of the backscattered light. Because of the multiple scattering of light in tissues by the red cells, neither the angle of incidence at any given red cell nor the angle of scattering of the light can be controlled by the geometry of the apparatus. In addition, at least some of the light may be scattered by more than one red cell, thereby sustaining more than one Doppler shift. For these reasons the spectrum of light scattered from a complex structure, such as a perfused kidney or the like, in theory at least cannot at present be exactly predicted. However, if the overall flow pattern is speeded up or slowed down, the overall linewidth of the spectrum will scale in the same way as the velocity distribution of the red cells, because this amounts in essence to changing the time scale of the flow pattern. This has been demonstrated experimentally for blood in capillary tubes, and applied with great generality.

If the scattered light is allowed to fall on a photodetector such as a photodiode or photomultiplier tube, the various Doppler shifted components beat with one another to produce fluctuations in the photocurrent at audio frequencies. If there is a dominant component of light scattered from stationary stroma, as is clearly true for skin, and true at least under some conditions for a renal cortex, this scattered light can serve as a reference carrier, and the spectrum of the beat frequencies will have the same shape as the spectral line of the light; that is, a heterodyne spectrum results. If all the scattered light comes from the red blood cells, the different Doppler components beat with one another and a homodyne spectrum results. This spectrum is the self-convolution of the heterodyne spectrum, and wider by a factor of $\sqrt{2}$. In either case, or any intermediate case in which both homodyne and heterodyne spectrums result and are superimposed as a composite spectrum, the composite photocurrent spectrum scales in width like the velocity distribution of red blood cells.

One measure of the linewidth is the root-mean-square (RMS) bandwidth $$F = \sqrt{\int P(\omega)\omega^2 d\omega} \qquad (1)$$

where $P(\omega)$ is the power spectrum of the photocurrent from a photodiode or photomultiplier tube. For laminar flow in fixed geometry, F is directly proportional to flow rate. In more general cases, it can be considered the product of G · $F_t$ true blood flow, the calibration "constant" G in each general case depending on the geometry of the flow and the optical properties of the tissue which is illuminated. Since the number F defined by equation (1) already varies directly with the amount of light scattered by red blood cells, and therefore with the amount of blood in the tissue, it scales like flow in this respect also, and it is reasonable to expect that the factor G will not vary greatly in any one tissue in the course of ordinary changes of physiologic state. This will certainly be the case for changes due to vasomotion occurring outside the region of observation and at localized sphincters which contain only a small faction of the red cells in the observation region.

These considerations make it plausible that the parameter F should vary, in a more or less linear fashion, with tissue blood flow in a given tissue; moreover, F can be measured continuously by simple analog circuitry not requiring a spectrum analyzer. As a practical matter, the flow parameter can be determined as an RMS flow parameter.

Referring to FIG. 1, the experimental set-up for studying local blood flow in the outer cortex of a kidney of a rat 10 includes a 15mW helium-neon laser 11 (Jodan Engineering model HN-15) which produces monochromatic, coherent light having a wave length of 632.8 nm and a beam width of approximately one mm. The light from the laser 11, as shown, impinges on a half-silvered mirror 12, which reflects the beam towards the exposed kidney of the rat 10, to illuminate a spot on the exposed renal cortex. The kidney is supported by a glass half-ring kidney support 13, which includes at least one rod member in contact with the surface which supports the rat 10. The support 13 prevents the kidney from moving to any appreciable degree during the procedure. The backscattered light passes firstly through a two mm aperture in a mask 14 at the surface of the kidney, thence through the half-silver mirror 12 to a second mirror 9 which directs the light which passes through the mirror 12 towards and through a 0.5 mm pinhole 15 located in a disc 16 positioned approximately one mm away from the mask 14. It is to be understood that a single, tilted, fully silvered mirror could be used in place of the two mirrors 9 and 12 and the members 16–18 somewhat differently positioned. The two mm aperture and the 0.5 mm pinhole restrict the scattered laser light so that approximately one coherent area of the renal cortex is sampled. It is to be understood that as a practical matter, light from the laser which impinges on the surface of the renal cortex at some distances from a single coherent area, does not have a coherent relationship to the light from the area sought to be sampled. The backscattered light which passes through the aperture 15 in the disc 16 is passed through an interference filter 17 which has a band width approximately 3 nm centered about 632.8 nm, the interference filter 17 centered about the wavelength serves the purpose of blocking ambient light so as to make the experimental set-up insensitive to ordinary room lights. The beam of coherent light which passes through the interference filter 17 is directed through lens 18 onto the photocathode of a photomultiplier tube 20 having a high quantum efficiency in the red (EMI 7658-R). While the photomultiplier tube 20 is utilized in the exemplary embodiment, it is to be appreciated that other types of photo-detectors, such as a photodiode could be used as well. The photomultiplier tube 20 like photodiodes, is a non-linear device. The various Doppler shifted components of the light which impinge of the cathode of the photomultiplier tube 20 beat with one another to produce fluctuations in the photocurrent output from the tube 20. The frequency relationships are such that audio frequency signals are produced as beat notes so as to provide either a homodyne spectrum, a heterodyne spectrum or mixed spectrum of audio frequencies, as indicated above. The beat frequency photocurrent output from the photomultiplier tube 20 is supplied to a preamplifier 21. The output from the preamplifier 21, in the experimental set-up is fed to an analog tape recorder 22, which records the output for possible further study. An output from the preamplifier 21 is also fed to an oscilloscope 23 and to an X-Y recorder 24 via a spectrum analyzer 25. The X-Y recorder serves the purpose of recording the output of the amplifier 25 for further study, while the oscilloscope 23 permits direct viewing of the spectrum during experiments.

In accordance with the apparatus of the present invention, the output from the preamplifier 21 is fed to an adjustable low pass filter 26, which passes, for example, frequencies of up to about 20 KHz. The output from the filter 26 is fed to a conventional differentiator 27 which differentiates the received audio frequency signals with respect to time. The differentiated output from the differentiator 27 is fed to a root-mean-square (RMS) detector 28. As shown, the output from the root-mean-square detector 28 is fed to a digital voltmeter 29, the output from the root-mean-square detector 28 being fed additionally to a first input of a flow parameter calculating circuit 30. The flow parameter calculating circuit 30 has a second input which is coupled to an output from a linear, averaging amplifier 31 which has its input coupled to the output of the preamplifier 21. The linear, averaging amplifier 31 is preferably adjustable and includes an RC feedback loop, and produces an output signal indicative of the mean photomultiplier tube current produced in the tube 20; this output is displayed on digital voltmeter 39.

Figure 8:
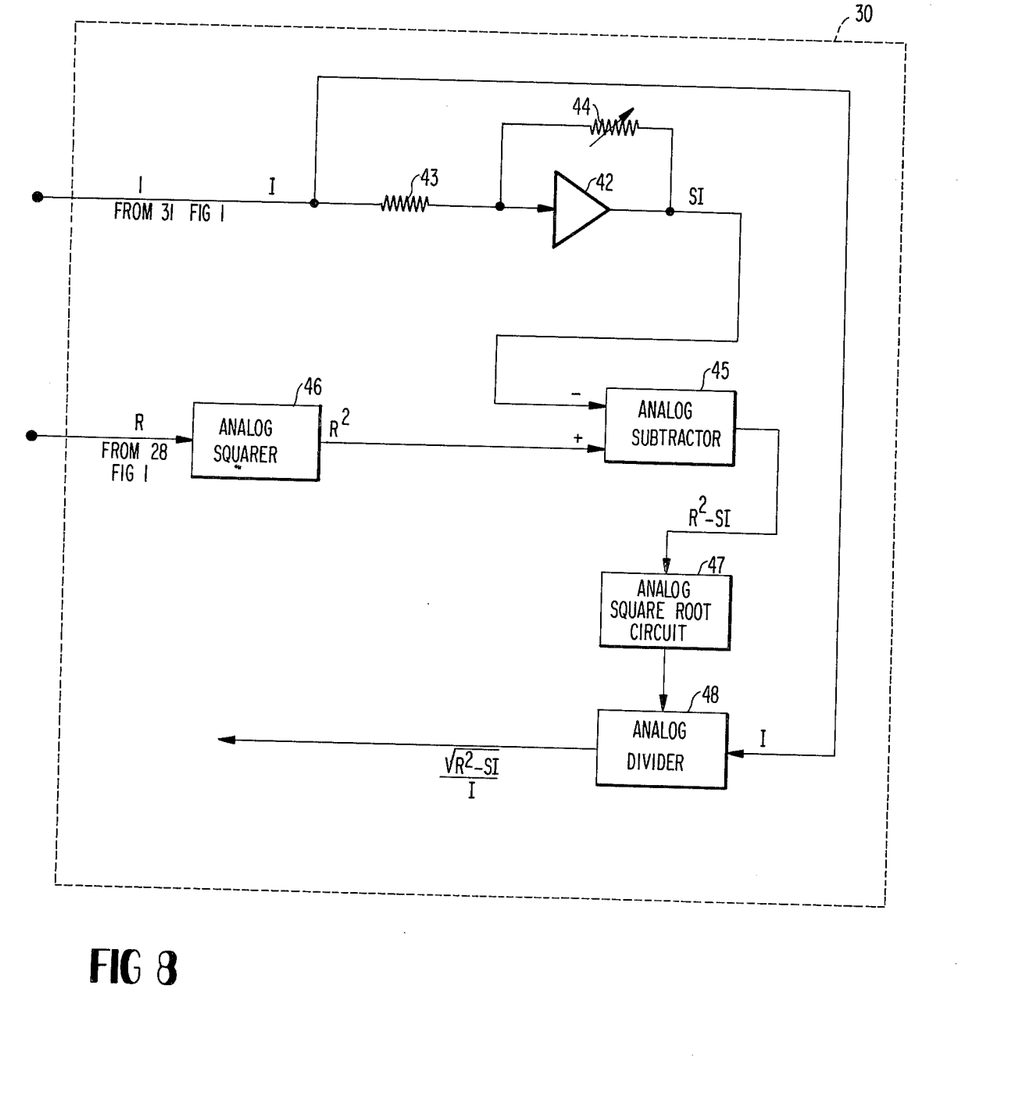
FIG. 8 is a schematic diagram of an analog calculation circuit suitable for use as the flow parameter calculation circuit shown in FIG. 1.

The flow parameter calculating circuit 30 is an arithmetic, analog circuit which produces an output representative of the flow parameter, preferably normalized. The details of construction and operation of the flow parameter calculating circuit 30 are to be considered further hereinbelow and are illustrated in FIG. 8.

The output from the root-mean-square detector 28 is fed as one input to a strip-chart recorder 32, which is provided with four additional inputs. The output signal from the linear averaging amplifier 31, which represents the mean photomultiplier tube current is fed to a second input to the strip-chart recorder 32.

The experimental setup includes additionally an EKG input to the strip-chart recorder 32 from conventional needle electrodes (not shown) operatively associated with the rat 10. A conventional rate monitor 33 (Hewlett-Packard 780 7A) is also connected to these electrodes to develop an output analog signal representing the heart beat rate. A pressure transducer in the form of a strain gauge monometer 34 (Statham P23 db) is coupled by a 0.023 inch ID polyetheylene tubing 35 to the carotid artery of the rat 10 so as to produce an output signal representative of the arterial blood pressure, this signal being coupled to a further input of the strip-chart recorder 32. The trachea of the rat 10 is cannulated with a 3 cm No. 12 thin walled polyethylene tubing 36. During experimental procedure using the setup illustrated in FIG. 1, the arterial blood pressure, EKG, analog heart rate, mean photomultiplier tube current and the root-mean-square detector output signals are continuously and simultaneously recorded for further study on the strip-chart recorder 32.

The infusion pumps 37 and 38 are connected respectively to the internal jugular vein and to the femoral vein of the rat 10 via a 0.11 inch ID polyethylene tubing 40 and appropriately sized polyethylene tubing 41 so that the rat may be infused or injected with various material during experimental procedures.

The actual photocurrent from the photomultiplier tube 20 contains, in addition to the flow signal, a certain irreducible amount of shot noise—noise which is due to the quantum nature of light, has a perfectly white spectrum, and is uncorrelated with the signal, to which it therefore adds in quadrature. Also, the total signal amplitude is proportional to the amount of light returned from the kidney of the rat 10, which may vary somewhat due to drift in power of the laser 11 and variations in the color of kidneys. To compensate for these effects, the actual, normalized flow parameter is computed by the calculating circuit 30 from the output of the root-mean-square detector 28 and from the linear amplifier 31 by the equation $$F_{norm} = \frac{\sqrt{R^2 - SI}}{I} \qquad (2)$$

where $R$ is the RMS detector output, $I$ is the mean photocurrent and $S$ is the shot noise constant. This assures, among other things, that the variations in F are not due to changes in the color of the tissue. It is to be understood that if a normalized output is not desired, the computation need not include the final arithmetic division by I. The shot noise constant $S$ depends on the gain of the photomultiplier tube 20. This may vary somewhat from day to day, as a practical matter $S$ can be determined before each experiment by zeroing the apparatus on a stationary object which will reflect the light from the laser 11. The zero set of the apparatus does not depend on any biological calibration. The zeroing of the apparatus is effected by simply adjusting a potentiometer in the calculating circuit 30 under conditions standard for the experiment to be conducted, with the laser light reflected solely from a motionless object instead of the kidney. No other smoothing or manipulation of the data is necessary.

The experimental setup illustrated in FIG. 1 was used in studying male Sprague-Dawley rats. The male Sprague-Dawley rats weighing 350–450 grams were anesthetized with Sodium Pentobarbital (Veterinary Laboratories) 6 mg/Kg intramuscularly. The trachea of each rat was cannulated with the 3 cm of No. 12 thin walled polyethylene tubing 36. The carotid artery on one side was cannulated with the 0.023 inch ID polyethylene tubing 35 and internal jugular vein cannulated with the 0.011 inch ID polyethylene tubing 40. When two drugs were to be infused simultaneously, the femoral vein was also cannulated, with the appropriately sized, polyethylene tubing 41. The left kidney was exposed by left abdominal approach, freed from underlying connective tissue by blunt dissection, supported on the glass half-ring support 13 and bathed in mineral oil at 37° C, as for micropuncture. The oil temperature was monitored continuously by a thermistor probe (not shown) at the end of an oil pipette (not shown). Arterial pressure was monitored with the strain gauge manometer 34 and recorder continuously on the strip chart of the recorded 32. The EKG was monitored via the conventional needle electrodes and recorded continuously on the strip-chart of the recorder 32, and heart rate was monitored by the standard rate monitor 33 connected to the strip-chart recorder 32 and to a frequency meter (Hewlett-Packard 500C).

Preparations were discarded in the event that mean blood pressure fell below 90 or the heart rate exceeded 350 under control conditions, or if there was significant bleeding or instability of physiologic parameters during control periods. There was no difficulty in distinguishing satisfactory preparations from unstable ones. Drugs were infused with the syringe infusion pumps 37 and 38 at flow rates not exceeding 0.05 ml/min intravenously. Comparable infusions of physiologic saline produced no effect.

A number of drugs were used in experiments with the setup shown in FIG. 1. These drugs included noreprinephrine (Levophed, Winthrop), hydralazine HCl (Apresoline, Ciba) angiotensin II amide (Hypertensin, Ciba), saralasin acetate (P113, Norwich) dopamine HCl (Intropin, Arnar-Stone), isoroterenol (Isuprel, Winthrop), dextran 70 (Macrodex, Pharmacia), epinephrine (Parke-Davis) and sodium nitroprusside (Nipride, Roche).

For those drugs which are rapid acting and rapidly metabolized (norepinephrine, angiotensin, epinephrine, dopamine, nitroprusside, isoproterenol) steady state intravenous dose response curves were obtained. The drug was infused at each dose rate until all physiologic parameters (including the Doppler shift parameter) reached steady state, at which time a reading was taken. Between points the animal being investigated was allowed to recover to a steady state at baseline values. Except in the case of animals found to be bleeding, which were discarded, the values always returned to baseline within 5% between infusions. The points on the dose response curve were taken in random order; doses were chosen empirically to include a full range from minimum threshold to a maximum rate which either produced a plateau of all physiologic response or intolerable side effects (e.g. cardiac arrhythmia, hypotension below 50 mmHg).

For long acting drugs (Hydralazine) the animal was allowed to achieve a steady baseline (variation in flow parameter of less than 5% over 30 minutes), following which single intravenous doses were given spaced to allow a plateau of all response before the next dose, in order to achieve a cumulative response curve. In the case of hydralazine, doses of 0.1 mg/Kg were given at intervals of 5 to 10 minutes until either a maximal increase in flow parameter was obtained, or mean blood pressure fell below 50 mm Hg. At that point the mean blood pressure was restored to 100 mm Hg by infusion of 6% dextran 70 solution (maximum 3 ml), and a further reading taken when steady state was established.

Kidneys in the control state gave rise to a spectrum of about 5 kHz width, of a shape and width consistent with theory. The flow parameter, in arbitrary units produced by the circuitry of the present invention, ranged between 1.12 and 1.4 for all the rates, usually being in the 1.25 to 1.35 range. The value varied by 5–8% from point to point over the exposed surface of the kidney, and fluctuated by less than 5% over 30 minutes of baseline. Rates in which the initial flow parameter was less than 1.0 turned out to have problems of preparation (bleeding, excessive anesthesia, etc.) which declared themselves in other ways during the control period; these rats were discarded.

If the rat was sacrificed by overdose of anesthesia, or if the renal pedicle was tied, the flow parameter immediately fell to 0.05 or less, and the spectrum became flat, as expected.

Figure 2:
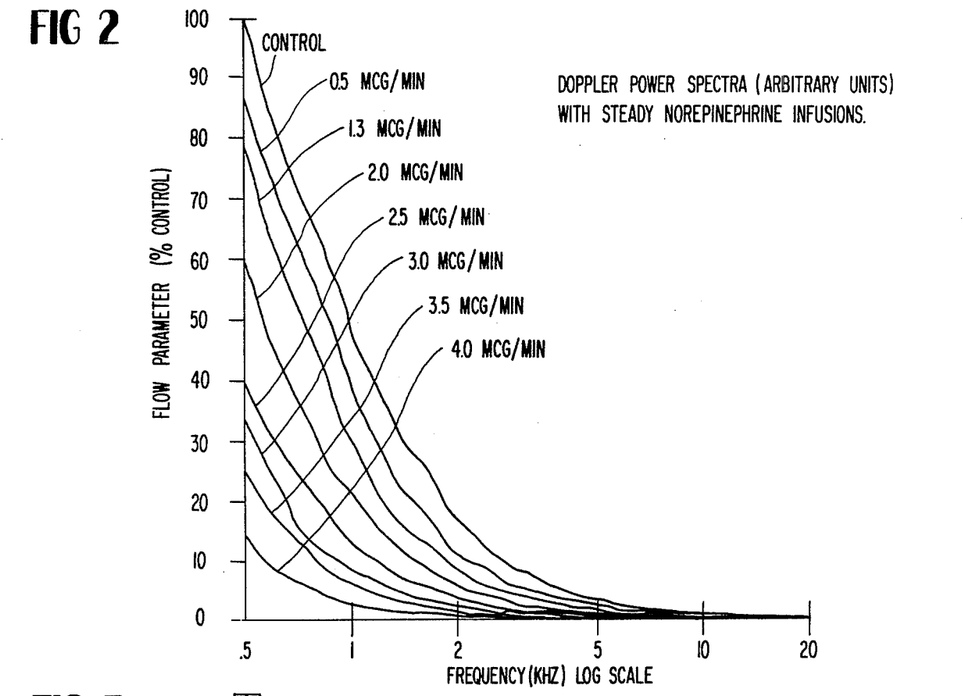
FIG. 2 is a graphical representation of a family of Doppler spectra obtained from the kidney of a rat using the apparatus of FIG. 1 while infusing the rat with norepinephrine.

FIG. 2 shows a typical family of light spectra obtained from the kidney in a given rat at various respective steady state infusion rates of norepinephrine infused intravenously. These spectra were obtained in random order, in real time, with return to the control spectrum between infusions. As indicated in FIG. 2, the infusion rates ranged from 0.5 to 4.0 MCG/min. Between the control state and the maximum infusion rate the mean blood pressure increased from 125 to 250 mm Hg, the heart rate from 280 to 420 and the flow parameter fell to 13% of its control value, chosen to equal 100 for the intercept of the control spectrum. The expected narrowing of the spectrum is seen with increasing vasoconstriction, as well as the characteristic logarithmic shape of the spectrum at the low frequency end.

Complete dose response curves obtained for norepinephrine in eight different rats has indicated that the flow parameter always falls monotonically as a function of dose rate, typically reaching 30–40% of control values at maximum tolerated steady state dose rates. In all these animals, except one, the curve has been convex, having an exponential shape, with variation of about a factor of 3 in the absolute sensitivities of different animals to the drug.

Figure 3:
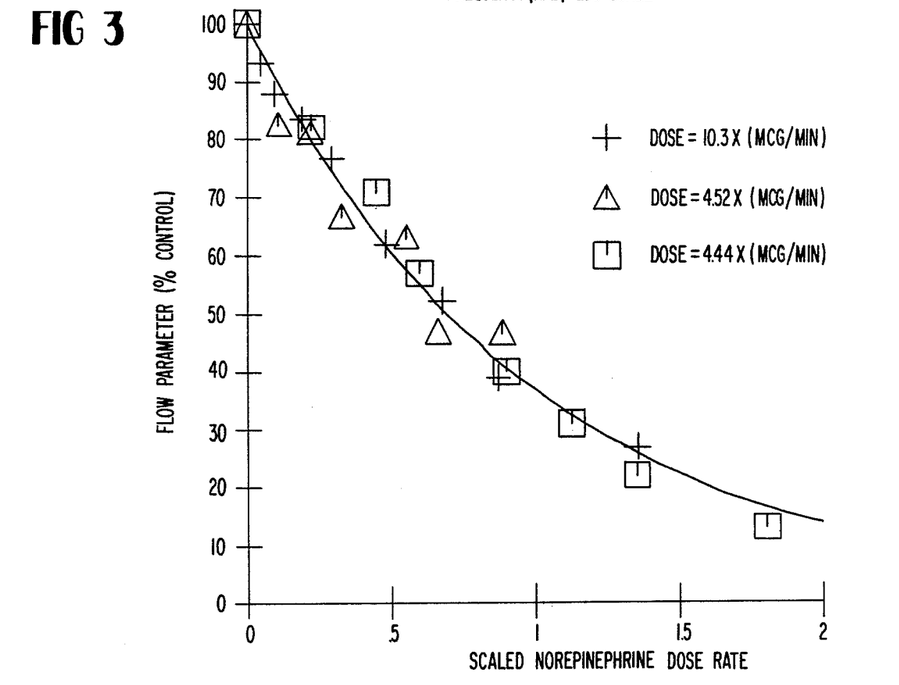
FIG. 3 is a graphical representation of steady state dose responses obtaining from the kidneys of three rats using the apparatus of FIG. 1, the rats having been intravenously supplied with norepinephrine.

In FIG. 3 the steady state dose response curves of the Doppler flow parameter to intravenous norepinephrine in three rats are shown, with the ordinate scaled as shown for each rat in order to fit a standard exponential curve. The flow parameter is shown on a percentage of the control value for each rat. It is noted that the curve is exponential.

Figure 4:
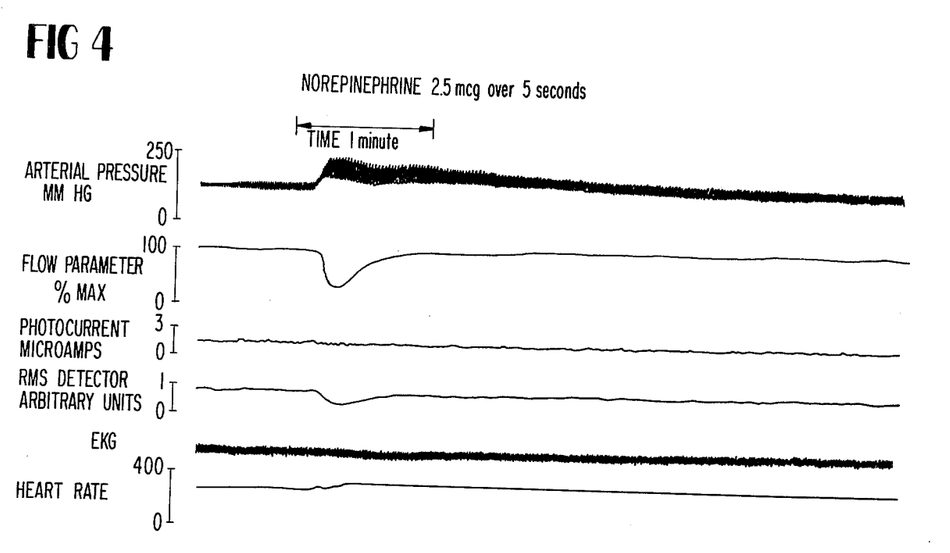
FIG. 4 is a graphical representation of physiologic data, including the transient response of the renal flow parameter, obtained from a rat using the apparatus of FIG. 1, over a period including a short span during which the rat was injected intravenously with norepinephrine.

In order to demonstrate the capacity of the Doppler technique to provide a rapid response, the norepinephrine was administered as a rapid intravenous bolus. A typical transient response to a moderate dose is shown in FIG. 4. Transient response to the laser renal flow parameter and other physiologic data to a bolus of 2.5 micrograms of norepinephrine injected intravenously over 5 seconds at the time shown by the vertical arrow in FIG. 4. The flow parameter is shown as percent of its control value prior to the injection. The mean photocurrent, an EKG, heart rate and the output of the root-mean-square detector from which the flow parameter is computed by the formula (2) set out hereinabove are shown as they were recorded by the strip-chart recorder 32 during this particular experiment. With higher bolus doses it is possible to reduce the flow parameter virtually to zero, as can be seen from FIG. 4, at the peak of the response. This cannot be done with steady state infusions due to occurrence of cardiac arrhythmias.

Figure 5A:
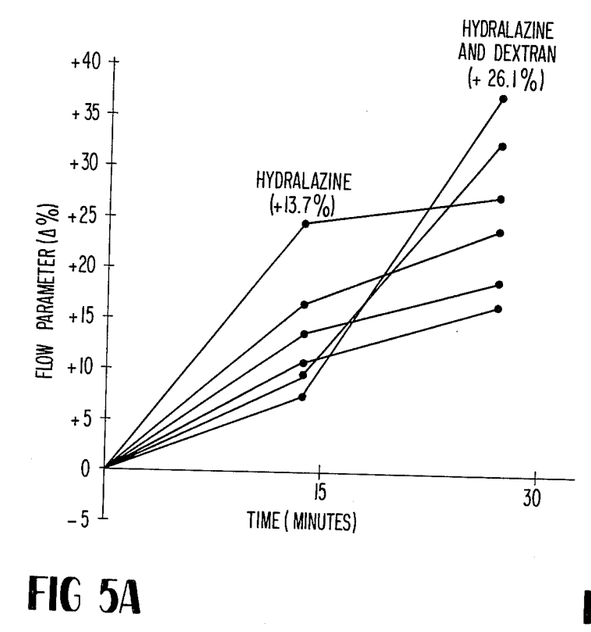
FIG. 5A and 5B are respectively graphical representations of renal cortical flow parameters in six rats under control state conditions and when subjected to hydrolazine given intravenously followed by dextran 70 obtained using the apparatus of FIG. 1.
Figure 5B:
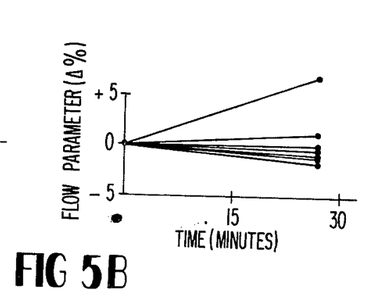

FIG. 5A shows graphically the percentage change in renal cortical flow parameter produced by hydralazine given intravenously to four rats, and by hydralazine followed by volume expansion with dextran 70 to restore mean arterial pressure to 100 mm Hg, in two rats; the changes produced by these interventions, compared to the control state immediately prior to injection of the same six rats as illustrated in FIG. 5B. The variations shown in FIG. 5B are random variations occurring over a comparable period (30 minutes) without intervention, in the same animals, prior to the first dose of hydralazine. The known renal vasodilator hydralazine was administered according to standard protocol. This typical response was an increase in the flow parameter up to a maximum, usually occurring at doses which lowered the mean blood pressure to about 80 mm Hg, followed by a decline at higher doses, if the blood pressure fell further, or a plateau if it did not. Restoring the blood pressure to 100 mm Hg by volume replacement produced a variable further increase in flow parameter. The maximum percentage change in flow parameter obtained with hydralazine, and with hydralazine plus the volume expansion in the six rats are shown in FIG. 5B, the differences are apparent.

Figure 6:
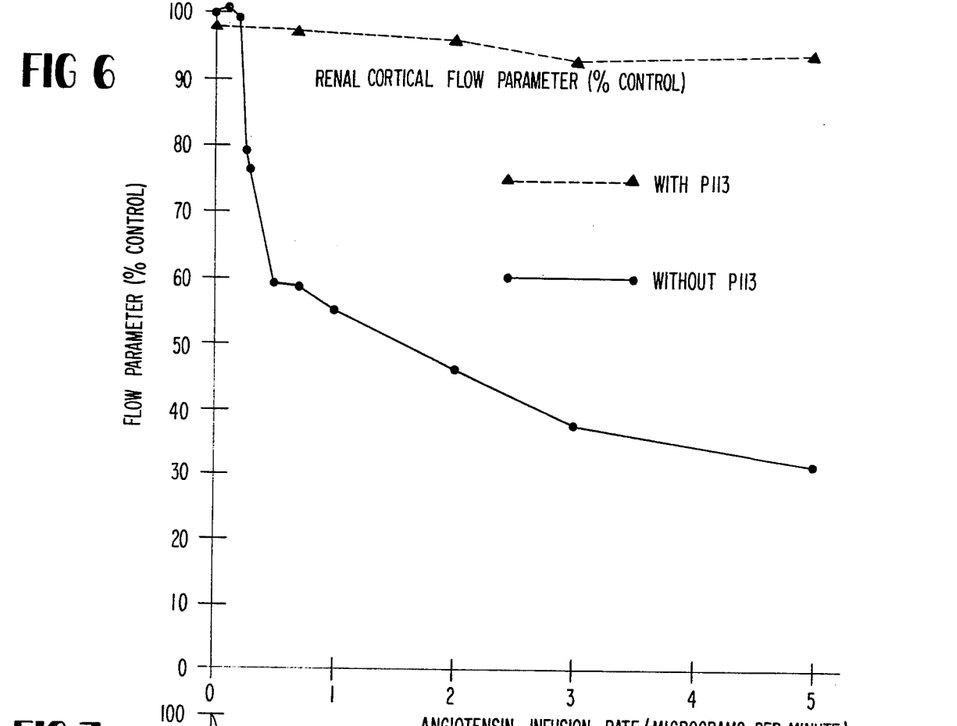
FIG. 6 is a graphical representation of renal cortical flow parameters, obtained from two rats, using the apparatus of FIG. 1, while subjecting the rats to intravenous angiotensin II, one of the rats being subjected simultaneously to infusion of the inhibitor saralasin (P113).

FIG. 6 shows graphically steady state dose response curves to intravenous angiotensin II obtained with and without a simultaneous infusion of the inhibitor saralasin (P113). The renal flow parameter on the vertical axis is expressed as a percentage of the control value obtained without either drug. All points were obtained in the same animal, in random order, with return to baseline between infusions. Angiotensin II was infused into the jugular vein at rates of 0–5 micrograms/minute which produced an increase in mean blood pressure from 100 to 180 mm Hg. A steady state dose response curve was obtained, with the points taken in random order. Each point was reproduced 2 or 3 times during the experiment with variation of less than 3%. A steady state infusion of saralasin, a competitive antagonist of angiotensin II, was given into the femoral vein at 25 micrograms/Kg/min, sufficient to maximally block the pressor effect of angiotensin at 5 micrograms/minute, and the angiotensin dose response curve was repeated. Saralasin alone produced no detectable pharmacologic effect, and the blood pressure and renal-flow effects of angiotensin were fully restored within 10 minutes following cessation of the saralasin infusion.

Epinephrine produced results qualitatively similar to norepinephrine in rats, as measured by the set-up shown in FIG. 1 showing pronounced vasoconstricting activity. The minimal flow parameter obtainable with steady state epinephrine was generally somewhat smaller than with norepinephrine.

Dopamine, isoproterenol, and nitroprusside were tested in 2–4 rats each and did not produce a significant effect on the renal flow parameter, as measured by the set-up shown in FIG. 1, at doses at which their other pharmacologic effects were pronounced. Isoproterenol produced a decrease in blood pressure, which reached minimum at intermediate dose rates and disappeared at higher dose rates, consistent with competition between peripheral and cardiac beta adrenergic effects. At the intermediate dose rates there was a slight (4%) decline in the renal flow parameter when the drug was given. Dopamine produced no change in the renal flow parameter over a range of doses which increased blood pressure from control values to 220 mm Hg. It was the only drug we tested which raised blood pressure without decreasing the renal flow parameter.

Figure 7:
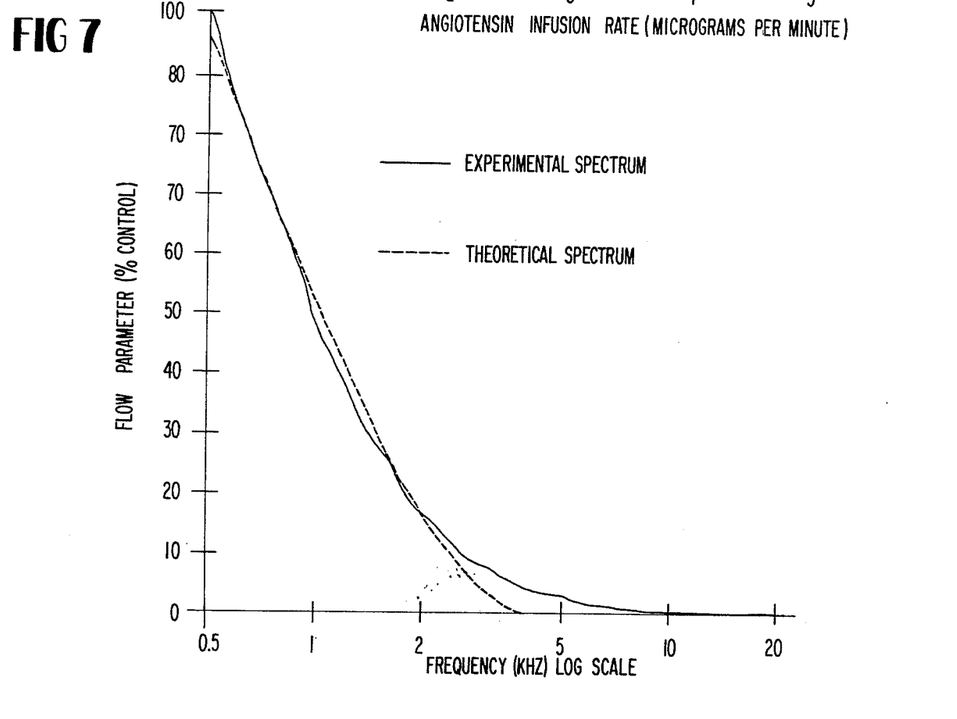
FIG. 7 is a graphical representation of an experimental spectrum like that of one of the curves shown in FIG. 2 and of an idealized theoretical spectrum obtained mathematically.

As illustrated in FIG. 7, a theoretical spectrum, based on an idealized theoretical model of equation (A9) set out hereinbelow comes very close to the control spectrum illustrated in FIG. 2, which has been illustrated in FIG. 7 as a solid line. The experimental spectrum shows the expected logarithmic behavior at low frequencies, and the expected high frequency "tail" suggesting that the idealized model is somewhat simplified.

The Doppler shift of light scattered from moving particles is determined by their absolute velocity, so that, in principal, one should be able to determine absolute tissue blood flow and velocity distribution from the Doppler spectrum. As a practical matter, the complexity of multiple scattering theory and uncertainties of the optical properties of tissues prevent a full theoretical interpretation of the spectrum, one must rely on a simplified analysis of the data, supported by general theory, and confirmed empirically. In the illustrative embodiment a root-mean-square average frequency shift as an indicator of flow has been chosen, because it is the easiest to obtain of the many possible weighted averages of the frequency shift which are linearly proportional to flow in the special case of laminar flow in a fixed geometry.

The flow parameter obtained from renal cortex is stable and reproducible and is quite sensitive to interventions which affect renal perfusion. The results of pharmacological intervention reported above should be interpreted in the light of the following relevant facts:

1. Norepinephrine and angiotensin are potent renal vasoconstrictors, which decrease flow approximately two fold when infused in the steady state, and probably do not affect intrarenal distribution, or else divert flow away from the outermost layer of the cortex (zone 1 of microsphere method); Rector et al. "Effect of hemorrhage and vasopressor agents on distribution of renal blood flow"; *Am. J. Phys.* Vol. 222, pp. 1125–1131, 1972.

2. Salalasin is an inhibitor of the vasopressor and renal vasoconstrictor effects of angiotensin II; Freeman et al. "Intrarenal role of angiotensin II. Hemeostatic regulation of renal blood flow in the dog"; *Circ. Res.* Vol. 32, pp. 692–698, 1973.

3. Hydralazine is known to increase renal blood flow, except at very low blood pressures, when its hypotensive effect overcomes renal vasodilation; Wilkinson et al. "Cardiovascular and renal adjustments to a hypotensive agent (1-hydrazinophthalazine; Ciba BA-5968: apresoline)"; *J. Clin. Invest.* Vol. 31, pp. 872–879, 1952.

4. Dopamine is a beta adrenergic and alpha adrenergic amine, which is also thought to have a direct renal vasodilating action: Goldberg, L. I., "Cardiovascular and renal action of dopamine: potential clinical applications"; *Pharm. Rev.* Vol. 24, pp. 1–29, 1972.

5. Renal vasodilators tend to divert flow away from the outermost zone of the renal cortex, resulting in only modest increases, or no change, in absolute flow to this region; Stein et al. "Effect of renal vasodilatation on the distribution of cortical blood flow in the kidney of the dog"; *J. Clin. Invest.* Vol. 50, pp. 1429–1438, 1971.

6. Isoproterenol is a beta adrenergic stimulant, with slight alpha receptor action.

7. The adrenergic receptors of the kidney are vasoconstrictor alpha receptors.

8. Sodium nitroprusside produces profound fall in blood pressure, due presumably to a direct vasodilating action in a wide range of systemic vessels; Bastron et al. "Effect of sodium nitroprusside on function in the isolated and intact dog kidney;" *J. Pharm. Exp. Therap.* Vol. 181, pp. 244–249, 1972.

9. The kidney is known to autoregulate blood flow over a wide range of perfusion pressures.

The penetration depth of the laser-produced light used in the exemplary embodiment of the present invention is difficult to determine precisely. In general, light scattered back from a diffusing object is expected to travel as far laterally as it penetrates in depth before re-emerging. Since greater than 50% of the total reflected light from the kidney emerges within a 1.5 mm diameter circle centered on the 1 mm laser spot, it is estimated that a penetration depth of 0.5 to 1 mm results. This would mean that most of the signal light comes from the outermost region (zone 1) of the cortex, a region thought to have a unique vascular architecture and reactivity; Forman et al. "Observations on the fine blood vessels of the kidney." *Cardiovascular Anatomy and Pathology*, ed. R. T. Harrison and K. R. Hill, New York, Academic Press, pp. 57–71, 1964. The behavior of our flow parameter in response to pharmacologic agents is consistent with the assumption that it is related in a relatively linear manner to outer zone blood flow. It is easier to obtain large decreases of the flow parameter than large increases above control state. This is consistent with the fact that most vasodilator drugs are thought to divert flow away from the outer zone. Nevertheless, it is possible that this asymmetry of response reflects a non-linearity in the response of our instrument at high flow states. Possible causes of non-linearity are significant inhomogeneity in the degree of vasomotion in different parts of the observed region, and changes in the effective vascular architecture due to the drugs themselves. The laser Doppler method measures an average "percolation" in the tissue; the ratio of this percolation to absolute rate of flow through the tissue obviously depends on the topology of the vascular bed. This is not expected to change greatly in the outer renal cortex during acute interventions.

The demonstration that saralasin blocked the effect of angiotensin on the renal flow parameter illustrates the kind of pharmacologic experiment which is easily performed using the laser Doppler method. The blockade of the renal effect of angiotensin on local outer cortical flow, while expected, is believed not to have been demonstrated before.

One possible source of error in practicing the present invention is motion of the kidney. If the kidney support 13 is hand-held, and the kidney gently waved back and forth about a millimeter every second, it has found that only a 5% error results in the flow parameter in control states, when measured in accordance with the present invention. Lower flow states are expected to be proportionally more sensitive to motion artifact. Motion artifact always increases the flow parameter (since motion noise adds in mean square), so the fact, that flow parameters as low as 5% of control have been obtained by giving a bolus of norepinephrine indicates relative insensitivity to motion under normal experimental conditions.

The laser technique has essentially instantaneous response and can be used to make an unlimited number of comparative measures of flow in a single animal. Whether it can be used to measure absolute flow will depend on the extent to which the calibration turns out to vary with the individual differences in renal vascular architecture, color of the kidney, etc. In view of the rather small variation in resting flow parameter from one animal to another, it is believed that measurement of absolute flow using the approach taught by the present invention may indeed be possible.

With the experimental set-up shown in FIG. 1, one is limited by the penetration depth of the light to the study of the outermost cortex. It is possible that greater depth of penetration could be achieved by working at longer wavelengths. In addition, another potential source of error, variation in the color of hemoglobin due to desaturation, could be eliminated by working at one of the isosbestic points in the spectrum of hemoglobin (such as 805 nm). It is to be appreciated that any number of wavelengths could be used, depending on the color of the tissue, cells or other materials in motion whose flow parameter is to be investigated.

While the set-up shown in FIG. 1 shows the use of two mirrors to illuminate and receive backscattered light from the region to be examined, and it is mentioned hereinabove that a single fully silvered mirror appropriately tilted can be used, it is to be appreciated that other more complex optics could be used. Moreover, in some applications fiber optics could be used; in which case, the light could be used to illuminate a tissue volume considerably beneath the surface and to collect and return the scattered Doppler shifted light. Similarly, surfaces of organs also could be examined without making any major incisions to obtain access to the organ.

A brief consideration of the theory of the spectrum and of a derivation of equation (2) is set out below.

If laser light is scattered by a single particle, such as a red blood cell, which is moving at a steady velocity over a distance long compared to the wavelength of light, the scattered light has its frequency shifted by the Doppler frequency $$\omega = \vec{K} \cdot \vec{V} \equiv Kv \cos \theta \tag{A1}$$

where $\vec{K}$ is the scattering vector of the light (defined as the difference of the wave vectors of the incident and scattered light), $\vec{V}$ is the velocity vector of the red cell, $v$ is the speed of the red cell (a scalar) and $\theta$ is the angle between the velocity vector and the scattering vector. In the case of light reflected from a multiple scattering medium containing many moving red cells, it is not possible at present to predict the shape of the spectrum theoretically in a practical way from scattering theory. In order to predict the general features expected for this spectrum, one may adopt the "wandering photon" model of the scattering process. This pictures the light as a stream of photons, which diffuse through the tissue by a random walk process, being multiply scattered by fixed stroma and one or more moving red cells. When the photon is scattered by a moving red cell, its frequency is shifted by an amount given by (A1). The rigorous justification of the photon wandering model is a very complex problem in the theory of multidimensional stochastic processes and are not here considered. In general, one can expect the model to apply when the volume of tissue sample is large compared to the distance over which the motion of red cells is correlated which is probably valid in the renal cortical microcirculation.

Under the wandering photon model, the spectrum of light from the tissue is composed of number of components corresponding to light which has been sequentially scattered by 1, 2 . . . different moving cells:

$$P(\omega) = P_1(\omega) + P_2(\omega) + \ldots \tag{A2}$$

The individual spectra $P_1 \ldots P_n \ldots$ are simply the probability distributions of the Doppler shift sustained by a photon which has encountered $n$ red cells, weighted according to the probability of the photon scattering from that many red cells before emerging. These probabilities diminish rapidly for higher order scattering, due to absorption of the light, so that the series (A2) converges.

Let one examine the first order term, the probability distribution of $\omega$ for light which has been scattered by a single red cell. The angles of incidence and scattering are random variables, as are the velocity and direction of the red cell. Considering first the case where K, the magnitude of the scattering vector, and $v$, the speed of the red cell, are fixed, then the variation of $\omega$ is due only to variation of the angle between the velocity vector and the scattering vector. One can make the assumption that the relative orientation of these two are random, which will be the case if the red cell velocities are distributed isotrophically, or the direction of the light is diffused before and after scattering by the red cell, or both. The probability of a given frequency shift will depend only on the solid angle subtended at the corresponding angle:

$$P_{Kv}(\omega) = \frac{d\Omega(\cos\theta)}{4\pi \, d\omega} = (\tfrac{1}{2}) \frac{\sin\theta \, d\theta}{d\omega} \tag{A3}$$

$$= (\tfrac{1}{2}) \frac{d}{d\omega} (\frac{\omega}{K_v}) = \frac{1}{2Kv}$$

Integrating over the true distribution of K and $v$ one finds $$P(\omega) = \int\int \frac{\rho(K) \, U(v)}{2Kv} \, dK \, dv \tag{A4}$$

where $\rho(K)$ is the probability distribution of K and $U(v)$ is the speed distribution of the red cells. The limits of integration in (A4) are defined by the possible values which K can take, and the possible values of $\omega$ which can occur with a given K and $v$ based on (A1):

$$0 \leq K \leq 2k \tag{A5}$$

$$|\omega| < Kv < \infty$$

where $k$ is the wave number $(2\pi/\lambda)$ of the light.

If one makes the substitution $z = Kv$ in (A5) one obtains $$P(\omega) = \int_\omega^\infty \int_0^{2k} \frac{\rho(K) \, U(k)(\frac{z}{K})}{2 \, Kz} \, dK \, dz \tag{A6}$$

Differentiating (A6) with respect to frequency gives $$\frac{dP(\omega)}{d\omega} = \frac{1}{2\omega} \int_0^{2k} \frac{\rho(K) \, U(\frac{\omega}{K})}{K} \, dK \tag{A7}$$

The value $K = 0$ corresponds to forward scattering. Since the scattering by randomly oriented red cells had cylindrical symmetry, scattering very close to forward has diminishing probability, so that $\rho(0) = 0$ and $\rho(K)/K$ tends to a finite limit as $K \to 0$. If the distribution $U(v)$ is attributed to an array of tubes carrying laminar flow at various speeds, then there will be a maximum speed of red cells, above which $U(v)$ goes to zero, and $U(v)$ will have a non-zero, finite value at $v = 0$. From these facts it is possible to deduce that the integral in eq (A7) tends to a finite limit as $\omega \to 0$, so that $P(\omega)$ behaves like $-\log(\omega)$ at low frequencies. For the idealized special case of an array of identical cylindrical vessels carrying the same flow in different directions, and red cells which scatter isotropically, the distributions are given by $$\rho(K) = \frac{K}{2k^2} \ ; \ U(v) = \begin{cases} \frac{1}{v_{max}} \\ 0 \end{cases} \quad (A8)$$

where $v_{max}$ is the central (maximum) flow speed in the vessels and we can integrate (A6) directly to find $P(\omega)$:

$$P(\omega) = \qquad (A9)$$

$$\begin{cases} \frac{1}{\omega_{max}} \left[ \ln\left(\frac{\omega_{max}}{\omega}\right) + \left(\frac{\omega - 1}{\omega_{max}}\right) \right] \\ 0 \text{ for } \omega > \omega_{max} \end{cases} \text{ for } \omega < \omega_{max}$$

where the maximum frequency in the spectrum is $$\omega_{max} = 2kv_{max} \qquad (A10)$$

In the more general case one can still expect from (A7) that a first order Doppler spectrum will have a logarithmic (integrable) singularity at low frequencies; it will have a log ($\omega$) term which dominates at low frequencies, and a high frequency "tail".

The $n$th order spectrum is proportional to the probability distribution of the random Doppler shift accumulated by one photon when scattered successively by $n$ red cells. If we assume that these successive shifts are statistically independent then $$P_n(\omega) = P^{(1)}(\omega) \otimes P^{(2)}(\omega) \otimes \ldots P^{(n)}(\omega) \qquad (A11)$$

where $P^{(K)}(\omega)$ is the first order spectrum of the shift produced by the $k$th red cell and "$\otimes$" indicates convolution. The individual $P^{(K)}$ spectra each consist of a logarithmic singularity and a finite tail which goes to zero at a maximum frequency. From this it can be shown (for example by Laplace transform methods) that the multiple convolutions $P_n(\omega)$ for $n > 1$ all have a finite limit as $\omega \to o$. The result of all this is that the first order term (with its log singularity) will dominate the total spectrum at low frequencies. Therefore, under relatively general assumptions it is expected that (1) the Doppler spectrum from tissue will vary as the negative logarithm of the frequency at low frequencies and (2) there will be a tail which goes to zero at high frequencies, which includes the effect of multiple scattering and the anisotropic scattering pattern of the red blood cells.

FIG. 7 shows an empirical spectrum at control flow (the same as the control spectrum from FIG. 2 and a theoretical spectrum based on the idealized first order solution in equation (A9). The value of $v_{max}$ and the overall amplitude scale of the theoretical spectrum have been chosen to give a least-squares fit. This illustrates the fact that the empirical spectrum has the general shape predicted in the preceding paragraph. The value of $v_{max}$ is 0.132 cm/sec, a reasonable order of magnitude for flow in microvessels. This should not be taken as a quantitative estimate of the flow speeds in a kidney, since the idealized assumptions used in deriving (A8) are clearly approximations to the true velocity distribution and red cell scattering pattern.

When Doppler broadened light is detected at a photomultiplier tube such as the tube 20, audio frequency fluctuations are produced in the photocurrent by the beat-frequencies of the different Doppler shifted components. Only light from nearby points of the scattering pattern can beat, since they are mutually coherent. The largest region (or coherent area) from which light can usefully contribute to the signal may be calculated from standard diffraction theory, and an appropriate pinhole is used to limit the light accepted by the photomultiplier to this region.

The spectrum of the photocurrent fluctuations consists of three components. The beat frequencies of the Doppler shifted light with light scattered by stationary tissues from the heterodyne spectrum, which has the same shape as the spectrum of the Doppler light itself. The beat frequencies of the Doppler shifted light with itself form the homodyne spectrum, which is the self-convolution of the heterodyne spectrum. The homodyne term scales in width proportional to the flow velocities, but it does not possess the logarithmic singularity of the heterodyne spectrum. The third term is shot noise. This is an inherent noise due to the quantum nature of light. It has a perfectly flat (white) spectrum, and is uncorrelated with the flow signal.

Suppose that one defines root-mean-square flow parameter as follows:

$$F = \sqrt{\int_o^\infty \omega^2 P(\omega) \, d\omega} \qquad (A12)$$

where $P(\omega)$ represents the flow signal spectrum (exclusive of shot noise). Suppose that the entire flow velocity distrubition were scaled by a factor $\alpha$ so that $v \to \alpha v$. This would occur if there were laminar flow through a fixed geometry at a flow rate which was varied by vasomotion outside the observed region. Then the velocity distribution and signal spectrum scale according to the relation $$U(v) \to \frac{1}{\alpha} U\left(\frac{v}{\alpha}\right);$$
$$P(\omega) \to \frac{1}{\alpha} P\left(\frac{\omega}{\alpha}\right) \qquad (A13)$$

Then the new value of the flow parameter is $$F\alpha = \sqrt{\int_o^\infty \frac{\omega^2}{\alpha} P\left(\frac{\omega}{\alpha}\right) d\omega} = \alpha \sqrt{\int_o^\infty \omega^2 P(\omega) \, d\omega} \qquad (A14)$$

so that the flow parameter scales in proportion to the increase in flow velocities. If the true tissue flow rate is $f_t$ then putting $\alpha = (f_t/f_o)$, where $f_o$ is some reference flow rate, $$F = f_t \left(\frac{F_o}{f_o}\right) \equiv G F_t \qquad (A15)$$

where $F_o$ is the value of the flow parameter in the reference state, and the calibration factor G is defined by (A15).

The computation of F from equation (A12) can be effected using a spectrum analyzer and a specially programmed computer. There is a much simper analog method of obtaining F. If the photocurrent is differentiated with respect to time, the power spectrum of the derivative is $$P_{diff}(\omega) = P_{exp}(\omega) \quad \text{(A16a)}$$

where $P_{exp}$ is comprised of the signal and the shot noise:

$$P_{exp}(\omega) = P(\omega) + NI \quad \text{(A16b)}$$

the latter being proportional to the mean photocurrent I. If the differentiated signal is passed through a low pass filter of cutoff frequency B where $B > \omega$ max, and then detected by a root-mean-square detector, the detector output is $$R = \sqrt{\int_0^B P_{diff}(\omega)\, d\omega} = \sqrt{\int_0^\infty \omega^2 P(\omega)\, d\omega + SI} = \sqrt{F^2 + SI} \quad \text{(A17)}$$

where the shot noise constant S is defined by $$S \equiv N \int_0^B \omega^2\, d\omega = \frac{NB^3}{3} \quad \text{(A18)}$$

Since S varies with the gain of the photomultiplier tube, it is determined empirically by placing a stationary object ($F = 0$) in the instrument. Finally, in order to cancel out the effect of variations in the amount of laser light, one can use the normalized flow parameter obtained by dividing F by the mean photocurrent:

$$F_{norm} = \frac{F}{I} = \frac{\sqrt{R^2 - SI}}{I} \quad \text{(A19)}$$

which is the same as equation (2) in the text.

As illustrated in FIG. 8, the flow parameter circuit 30 (FIG. 1) includes an operational amplifier 42 having its input terminal connected to the output terminal of the mean photomultiplier current amplifier 31 (FIG. 1), via a series connected resistor 43, to receive a signal I corresponding to the mean photocurrent. A manually adjustable, variable resistance 44 is connected between the output terminal and the input terminal of the amplifier 42, the resistance 44 serving the purpose of setting the feedback to provide a feedback signal to account for the shot noise constant S. Thus, the output signal from the operational amplifier 42 is a signal representative of SI when the variable resistance 44 has been appropriately adjusted.

An analog subtraction circuit 45 has its negative input terminal connected to the output terminal of the amplifier 42 for receiving the representative SI signal therefrom, its other positive input terminal being connected to the output terminal from an analog squarer 46 to receive the $R^2$ representing signal therefrom. The input terminal of the analog squarer 46 is connected to the output terminal of the root-mean-square detector 28 so as to receive the representative signal R therefrom and for producing the $R^2$ representing signal. The subtraction circuit 45 accordingly produces, as its output signal, a signal corresponding to $R^2 - SI$.

The $R^2 - SI$ representing output signal from the subtracting circuit 45 is fed to the input terminal of a conventional analog square root circuit 47 which produces an output signal corresponding to $\sqrt{R^2 - SI}$ which, in turn, is fed to a first, input terminal of a conventional, analog dividing circuit 48 which receives, at its other input terminal, the output signal from the amplifier 31 (FIG. 1) which represents the mean photomultiplier tube current I. The analog dividing circuit 48 produces, as its output signal, a signal representative of the normalized flow parameter which, as stated hereinabove, is defined as $$F_{norm} = \frac{\sqrt{R^2 - SI}}{I}.$$

Of course, if a normalized output is not desired, the dividing circuit 48 may be removed and the output from the square root circuit 47 used.

It is to be appreciated that the illustrative embodiments hereinabove described have been set out by way of example and not by way of limitation. It is to be understood that other embodiments and variants are possible, without departing from the spirit and scope of the invention, its scope being defined by the appended claims.

What is claimed is:

1. An apparatus for measuring blood flow in a vascular bed, the apparatus comprising:
   means for illuminating a region of tissue having a vascular bed with coherent light;
   means responsive to light backscattered from the region of tissue for producing a broadened spectrum signal output;
   circuit means coupled to said means for producing a broadened spectrum signal output and responsive to its broadened spectrum signal output for producing a signal representative of the blood flow in the vascular bed;
   means for collecting backscattered light from the region of tissue;
   wherein said means responsive to backscattered light comprise photo-detector means responsive to the collected light for developing a broadened spectrum of low frequency signals, said photo-detector means producing a means current and having a substantially constant shot noise output S;
   wherein said circuit means comprise means coupled to said photo-detector means and responsive to its output for developing an output signal I representative of the mean current thereof, weighted detector means coupled to said photo-detector and responsive to the broadened spectrum of low frequency signals for developing an output signal R; and calculating circuit means coupled to said weighted detector means and to said means for developing an output signal I and responsive to outputs thereof for producing an output signal F representative of the blood flow in the vascular bed.

2. An apparatus according to claim 1, wherein said calculating circuit comprises circuit means for producing an output signal F equal to $\sqrt{R^2 - SI}$ as a representation of blood flow parameter in the vascular bed.

3. An apparatus according to claim 1, wherein said calculating circuit comprises circuit means for producing an output signal $F_{norm}$ equal to $$\frac{\sqrt{R^2 - SI}}{I}$$

as a representation of blood flow parameter in the vascular bed.

4. An apparatus according to claim 1, wherein said means for illuminating a region of tissue comprises a laser.

5. An apparatus according to claim 4, wherein said laser is a He-Ne laser.

6. An apparatus according to claim 4, wherein said laser is a laser which produces coherent light having a wave length of substantially 632.8 nm.

7. An apparatus according to claim 4, wherein said laser is a laser which produces light having a wave length of substantially 805 nm.

8. An apparatus according to claim 1, wherein said photo-detector means comprises a photomultiplier tube.

9. An apparatus according to claim 1, wherein said means for developing an output signal I comprises amplifier means coupled to said photo-detector means.

10. An apparatus according to claim 9, wherein said amplifier means comprises a linear amplifier having an adjustable gain.

11. An apparatus according to claim 1, wherein said weighted detector means is a root-mean-square detector.

12. An apparatus for measuring blood flow in a vascular bed, the apparatus comprising:
means for illuminating a region of tissue having a vascular bed with coherent light;
means responsive to light backscattered from the region of tissue for producing a broadened spectrum signal output;
circuit means coupled to said means for producing a broadened spectrum signal output and responsive to its broadened spectrum signal output for producing a signal representative of the blood flow in the vascular bed; and
means for collecting backscattered light from the region of tissue;
wherein said means responsive to backscattered light comprise photo-detector means responsive to the collected light for developing a broadened spectrum of low frequency signals, said photo-detector means producing a mean current and having a substantially constant shot noise output S;
wherein said circuit means comprise means coupled to said photo-detector means and responsive to its output for developing an output signal I representative of the mean current thereof, weighted detector means coupled to said photodetector and responsive to the broadened spectrum of low frequency signals for developing an output signal R; including calculating circuit means coupled to said weighted detector means and to said means for developing an output signal I and responsive to outputs thereof for producing an output signal F representative of the blood flow in the vascular bed, and
a differentiator means and a low pass filter connected between said photo-detector means and said weighted detector means.

13. An apparatus according to claim 12, wherein said low pass filter is connected between said photo-detector means and said differentiator means, said differentiator means having its output coupled to said weighted detector means for differentiating signals received from said low pass filter means with respect to time and supplying these differentiated signals to said weighted detector means.

14. An apparatus according to claim 13, wherein said low pass filter is an adjustable filter for passing frequencies up to about 20 KHz.

15. A method of measuring the blood flow in a vascular bed, the method comprising:
illuminating a region of tissue having a vasuclar bed with coherent light;
collecting at least some of the scattered light from the region;
detecting the collected light to determine its broadened spectrum; and
determining the blood flow in the vascular bed from said broadened spectrum;
wherein said detecting step comprises non-linearly detecting the backscattered light in a photo-detector to produce a broadened spectrum of low frequency signals and a mean current signal I; and
wherein the determining step comprises producing a weighted output signal R from the broadened spectrum of low frequency signals, determining the shot noise constant S of the photo-detector, and producing a signal representation F, from the shot noise constant, the weighted output signal R and the mean current signal I.

16. A method according to claim 15, wherein the illuminating step comprises illuminating a region tissue having a microvascular bed, the collecting step comprises collecting at least some of the scattered light from the microvascular bed, and the determining step comprises determining the flow of red blood cells in the microvascular bed from said broadened spectrum.

17. A method according to claim 15, wherein the producing step comprises producing an output F equal to $\sqrt{R^2 - SI}$ as a representation of blood flow parameter in the vascular bed.

18. A method according to claim 15, wherein the producing step comprises producing a normalized output $F_{norm}$ equal to $$\frac{\sqrt{R^2 - SI}}{I}$$

as a representation of blood flow parameter in the vascular bed.

19. A method according to claim 15, wherein said illuminating step comprises illuminating a region of the tissue with coherent light having a wave length of substantially 632.8 nm.

20. A method according to claim 15, wherein said illuminating step comprises illuminating a region of the tissue with coherent light having a wave length of substantially 805 nm.

21. A method according to claim 15, wherein the step of detecting the broadened spectrum of low frequency signals comprises detecting the broadened spectrum of low frequency signals to produce a root-mean-square output signal R.

22. A method according to claim 15, including filtering the broadened spectrum of low frequency signals to pass only signals below a given frequency prior to detecting the broadened spectrum of low frequency signals.

23. A method of measuring the blood flow in a vascular bed, the method comprising:
  illuminating a region of tissue having a vascular bed with coherent light;
  collecting at least some of the scattered light from the region;
  detecting the collected light to determine its broadened spectrum;
  determining the blood flow in the vascular bed from said broadened spectrum;
  wherein said detecting step comprises non-linearly detecting the backscattered light in a photo-detector to produce a broadened spectrum of low frequency signals and a mean current signal I; and wherein the determining step comprises producing a weighted output signal R from the broadened spectrum of low frequency signals, determining the shot noise constant S of the photo-detector, and producing a signal representation F, from the shot noise constant, the weighted output signal R and the mean current signal I;
  filtering the broadened spectrum of low frequency signals to pass only signals below a given frequency prior to detecting the broadened spectrum of low frequency signals; and
  differentiating the filtered low frequency signals with respect to time prior to detecting the broadened spectrum of low frequency signals.

24. An apparatus for measuring the flow of flowing material, the apparatus comprising:
  means for illuminating at least a portion of the flowing material with coherent light;
  means for collecting backscattered light from the material;
  photo-detector means responsive to the collected light for developing a broadened spectrum of low frequency signals, said photo-detector means producing a mean current and having a substantially constant shot noise output S;
  means coupled to said photo-detector means and responsive to its output for developing an output signal I representative of the mean current thereof;
  weighted detector means coupled to said photo-detector and responsive to the broadened spectrum of low frequency signals for developing an output signal R; and
  calculating circuit means coupled to said weighted detector means and to said means for developing an output signal I and responsive to outputs thereof for producing an output signal F representative of the flow.

25. An apparatus according to claim 24, wherein said calculating circuit comprises circuit means for producing an output signal F equal to $\sqrt{R^2 - SI}$ as a representation of flow parameter.

26. An apparatus according to claim 24, wherein said calculating circuit comprises circuit means for producing an output signal $F_{norm}$ equal to $$\frac{\sqrt{R^2 - SI}}{I}$$

as a representation of flow parameter.

27. An apparatus according to claim 24, wherein said photo-detector means comprises a photomultiplier tube.

28. An apparatus according to claim 24, wherein said means for developing an output signal I comprises amplifier means coupled to said photo-detector means.

29. An apparatus according to claim 28, wherein said amplifier means comprises a linear amplifier having an adjustable gain.

30. An apparatus according to claim 24, wherein said weighted detector means is a root-mean-square detector.

31. An apparatus for measuring the flow of flowing material, the apparatus comprising:
  means for illuminating at least a portion of the flowing material with coherent light;
  means for collecting backscattered light from the material;
  photo-detector means responsive to the collected light for developing a broadened spectrum of low frequency signals, said photo-detector means producing a mean current and having a substantially constant shot noise output S;
  means coupled to said photo-detector means and responsive to its output for developing an output signal I representative of the mean current thereof;
  weighted detector means coupled to said photodetector and responsive to the broadened spectrum of low frequency signals for developing an output signal R;
  calculating circuit means coupled to said weighted detector means and to said means for developing an output signal I and responsive to outputs thereof for producing an output signal F representative of the flow; and
  a differentiator means and a low pass filter connected between said photo-detector means and said weighted detector means.

32. An apparatus according to claim 31, wherein said low pass filter is connected between said photo-detector means and said differentiator means, said differentiator means having its output coupled to said weighted detector means for differentiating signals received from said low pass filter means with respect to time and supplying these differentiated signals to said weighted detector means.

33. An apparatus according to claim 32, wherein said low pass filter is an adjustable filter for passing frequencies up to about 20 KHz.

34. A method of measuring the flow parameter of flowing material, the method comprising:
  illuminating at least a portion of the flowing material with coherent light;
  collecting at least some of the light scattered from the material;
  non-linearly detecting the collected light in a photo-detector to produce a broadened spectrum of low frequency signals and a mean current signal I;
  detecting the broadened spectrum of low frequency signals to produce a weighted output signal R;
  determining the shot noise constant S of the photodetector; and
  producing a signal representation F, from the shot noise constant, the weighted output signal R and the mean current signal I.

35. A method according to claim 34, wherein the producing step comprises producing an output F equal to $\sqrt{R^2 - SI}$ as a representation of flow parameter.

36. A method according to claim 34, wherein the producing step comprises producing a normalized output $F_{norm}$ equal to $$\frac{\sqrt{R^2 - SI}}{I}$$

as a representation of flow parameter.

37. A method according to claim 36, wherein the step of detecting the broadened spectrum of low frequency signals comprises detecting the broadened spectrum of low frequency signals to produce a root-mean-square output signal R.

38. A method according to claim 34, including filtering the broadened spectrum of low frequency signals to pass only signals below a given frequency prior to detecting the broadened spectrum of low frequency signals.

39. A method of measuring the flow parameter of flowing material, the method comprising:
- illuminating at least a portion of the flowing material with coherent light;
- collecting at least some of the light scattered from the material;
- non-linearly detecting the collected light in a photodetector to produce a broadened spectrum of low frequency signals and a mean current signal I;
- detecting the broadened spectrum of low frequency signals to produce a weighted output signal R;
- determining the shot noise constant S of the photodetector;
- producing a signal representation F, from the shot noise constant, the weighted output signal R and the mean current signal I;
- wherein the step of detecting the broadened spectrum of low frequency signals comprises detecting the broadened spectrum of low frequency signals to produce a root-mean-square output signal R;
- filtering the broadened spectrum of low frequency signals to pass only signals below a given frequency prior to detecting the broadened spectrum of low frequency singals, and
- differentiating the filtered low frequency signals with respect to time prior to detecting the broadened spectrum of low frequency signals.

* * * * *

UNITED STATES PATENT OFFICE
CERTIFICATE OF CORRECTION

Patent No. 4,109,647             Dated August 29, 1978

Inventor(s) Michael D. Stern et al.

It is certified that error appears in the above-identified patent and that said Letters Patent are hereby corrected as shown below:

Column 7, line 68, "recorded" should read -- recorder --.

Signed and Sealed this

Twenty-fourth Day of April 1979

[SEAL]

Attest:

RUTH C. MASON
Attesting Officer

DONALD W. BANNER
Commissioner of Patents and Trademarks